United States Patent
Bills (10) Patent No.: US 7,226,289 B2
(45) Date of Patent: Jun. 5, 2007

(54) METHOD FOR OVERMOLDING POLYMERS OVER DENTAL TOOLS

(75) Inventor: Dan J. Bills, West Jordan, UT (US)

(73) Assignee: Ultradent Products, Inc., South Jordan, UT (US)

(*) Notice: Subject to any disclaimer, the term of this patent is extended or adjusted under 35 U.S.C. 154(b) by 91 days.

(21) Appl. No.: 10/996,100

(22) Filed: Nov. 23, 2004

(65) Prior Publication Data

US 2006/0110703 A1 May 25, 2006

(51) Int. Cl.
*A61C 5/02* (2006.01)
(52) U.S. Cl. .................... 433/102; 433/224
(58) Field of Classification Search .......... 433/102, 433/141, 165, 224
See application file for complete search history.

(56) References Cited

U.S. PATENT DOCUMENTS

| | | | | |
|---|---|---|---|---|
| 4,155,964 A | 5/1979 | Aronow | ................ | 264/13 |
| 4,321,040 A | 3/1982 | Miller et al. | ............... | 433/102 |
| 4,535,014 A | 8/1985 | Wright | ................ | 428/30 |
| 4,759,713 A | 7/1988 | Heiss et al. | ............... | 433/141 |
| 4,942,791 A * | 7/1990 | Stewart et al. | ............. | 81/177.1 |
| 5,089,183 A * | 2/1992 | Johnson | ................ | 264/16 |
| 5,342,284 A * | 8/1994 | Lemon et al. | ............ | 601/141 |
| 5,390,572 A | 2/1995 | Gakhar et al. | .............. | 81/436 |
| 5,501,597 A | 3/1996 | Wilson | ............... | 433/141 |
| 5,516,287 A | 5/1996 | Zdarsky | ............... | 433/102 |
| 5,735,691 A * | 4/1998 | Fetter | ................ | 433/140 |
| 5,775,346 A * | 7/1998 | Szyszkowski | ............. | 132/329 |
| 5,956,799 A | 9/1999 | Panaccione et al. | ...... | 15/236.01 |
| 6,138,313 A | 10/2000 | Barton et al. | ............. | 15/143.1 |
| 6,213,771 B1 | 4/2001 | Fischer | ................ | 433/75 |
| 6,257,887 B1 | 7/2001 | Heckerman et al. | ........ | 433/141 |
| 6,276,020 B1 | 8/2001 | Leversby et al. | .......... | 15/167.1 |
| 6,295,903 B1 | 10/2001 | Tipper et al. | ................. | 81/489 |
| 6,305,937 B1 | 10/2001 | Williams | .................. | 433/141 |
| 6,322,362 B1 | 11/2001 | Holms | ................ | 433/143 |
| 6,322,738 B1 | 11/2001 | Sicilia et al. | .............. | 264/255 |
| 6,353,958 B2 | 3/2002 | Weihrauch | ................ | 15/167.1 |
| 6,368,536 B1 | 4/2002 | Hoepfl et al. | ............... | 264/250 |
| 6,401,290 B1 | 6/2002 | Barton et al. | ............ | 15/143.1 |
| 6,446,640 B1 * | 9/2002 | Gekhter et al. | .......... | 132/309 |
| 6,805,557 B2 * | 10/2004 | Davies et al. | ............. | 433/215 |
| 2003/0203155 A1 | 10/2003 | Kobe et al. | ............... | 428/119 |
| 2004/0091714 A1 | 5/2004 | Gunn | ................ | 428/421 |
| 2005/0221256 A1 * | 10/2005 | Kangasniemi | ............. | 433/102 |
| 2006/0063130 A1 * | 3/2006 | Hayman et al. | ........... | 433/141 |

* cited by examiner

*Primary Examiner*—Ralph A. Lewis
(74) *Attorney, Agent, or Firm*—Workman Nydegger (57) ABSTRACT

A method for overmolding a plurality of polymers having different properties onto a dental instrument. The method involves providing a dental instrument substrate made of metal, overmolding a first polymer onto a portion of the dental instrument substrate, and then applying a second polymer over a portion of the first polymer. The first polymer, which is advantageously rigid, is overmolded so that an exposed outer surface of the first polymer corresponds to a portion of the dental instrument to be gripped within a collet of a dental hand piece for powered use. The second polymer, which is advantageously soft and flexible, is applied so that an exposed outer surface of the second polymer corresponds to a portion of the dental instrument to be gripped by a dental practitioner for manual use.

24 Claims, 5 Drawing Sheets

METHOD FOR OVERMOLDING POLYMERS OVER DENTAL TOOLS

BACKGROUND OF THE INVENTION

1. The Field of the Invention

The invention is in the field of dental instruments. More particularly, the invention is in the field of processes for overmolding one or more polymers onto dental instruments (e.g., endodontic files).

2. The Relevant Technology

Dental instruments are often designed to be manually manipulated or to be fitted within a collet of a powered hand piece that provides rotation of an instrument during use. A dental instrument (e.g., an endodontic file) that is intended for hand use is typically provided with an enlarged diameter plastic handle attached to the proximal end of the instrument, configured for manipulation between the thumb and forefinger of the dental practitioner. An instrument intended for use with a powered hand piece has a stem at the instrument proximal end configured to be removably received within a collet of the powered hand piece, by which the instrument may then be rotated as desired by a dental practitioner.

It may be desirable for the enlarged plastic handle of a dental instrument intended for hand use to have a gripable surface. At the same time, dental instruments intended for use with a powered hand piece must include a rigid handle that can be received within a collet.

It would be an improvement in the art to provide a method of overmolding a handle onto a dental instrument, where the handle is suitable for manipulation by hand and by a powered hand piece.

BRIEF SUMMARY OF THE INVENTION

The present invention provides a method for overmolding a plurality of polymers having different properties onto a dental instrument. The method involves providing a dental instrument substrate made of metal, overmolding a first polymer onto a portion of the dental instrument substrate, and then applying a second polymer over a portion of the first polymer. The first polymer is overmolded so that an exposed outer surface of the first polymer corresponds to a portion of the dental instrument to be gripped within a collet of a dental hand piece for powered use. The second polymer is applied so that an exposed outer surface of the second polymer corresponds to a portion of the dental instrument to be gripped by a dental practitioner for manual use.

According to one embodiment, the first polymer may comprise a rigid polymer material. A rigid polymer material provides strength and durability, which is important for portions of the dental instrument that will be subjected to stresses and forces associated with gripping the instrument within the collet of a dental hand piece. Strength and durability will prevent these portions of the dental instrument from cracking or being deformed under stress. According to one embodiment, the rigid polymer material may comprise either a rigid thermoplastic or a rigid chemical cure or thermocure polymer material.

According to one embodiment, the second polymer may comprise an elastomeric material. An elastomeric material provides increased comfort and grippability to portions of the dental instrument that are gripped by a dental practitioner when using the dental instrument manually. According to one embodiment, the elastomeric polymer material may comprise either a thermoplastic elastomer or an elastomeric chemical cure or thermocure polymer material.

The resulting dental instrument includes portions having characteristics of rigidity, strength, and durability, and other portions having characteristics of elasticity, comfort, and grippability. These characteristics allow the dental instrument manufactured according to the inventive method to be used advantageously with a powered hand piece or manually, as desired.

According to one embodiment, the first polymer and second polymer are overmolded and applied respectively so as to form a handle having a trilobular cross sectional configuration. A handle having a trilobular cross sectional configuration is advantageous when manipulating the instrument by hand as it allows the dental practitioner to more easily apply the needed torque. In addition, a trilobular cross sectional configuration also provides improved gripability. A trilobular cross section may also be suitable for use within a powered hand piece.

According to one embodiment, the dental instrument manufactured according to the inventive method may be autoclavable. This may be accomplished according to one embodiment by selecting first and second polymers that are chemically or thermally curable and that have melting and decomposition temperatures that are significantly greater than autoclaving temperatures, which are typically 143° C.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which.

DETAILED DESCRIPTION OF THE PREFERRED EMBODIMENTS

I. Introduction

A detailed description of the inventive method and exemplary inventive dental instruments will now be provided, with specific reference to FIGS. 1-4 illustrating preferred embodiments of the invention. It will be appreciated that like structures will be provided with like reference designations.

II. Exemplary Methods of Overmolding Polymers Onto Dental Instruments

Figure 1A:
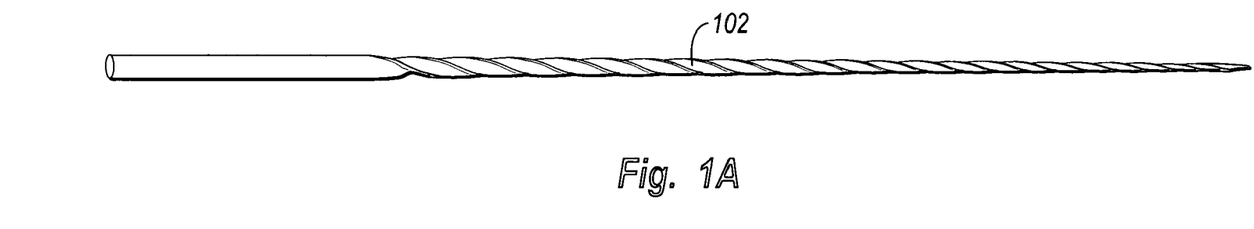
FIG. 1A is a perspective view of a dental instrument substrate made of metal.
Figure 1B:
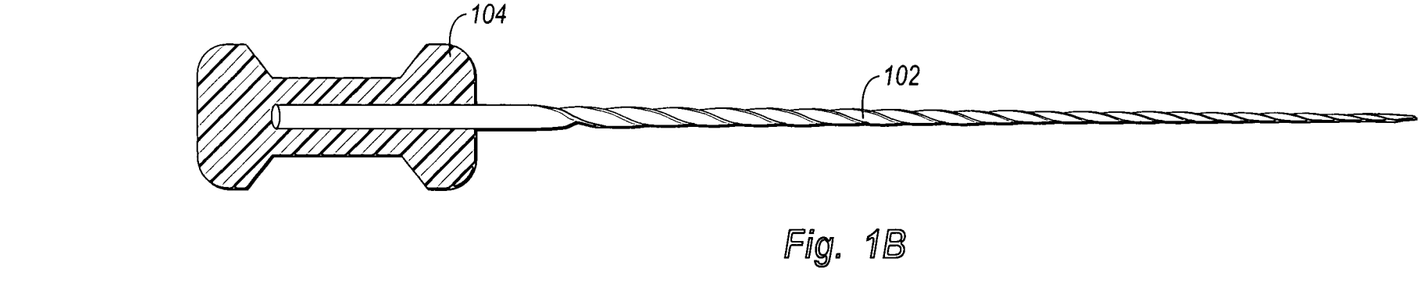
FIG. 1B is a cross sectional view of the dental instrument substrate of FIG. 1A with a first polymer overmolded onto a portion of the dental instrument substrate.
Figure 1C:
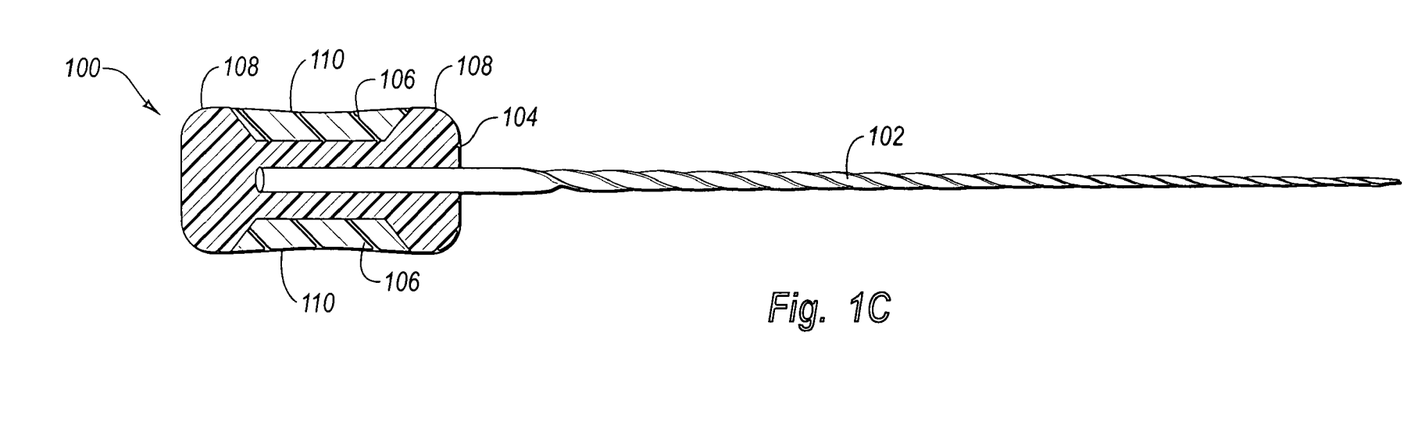
FIG. 1C is a cross sectional view of the dental instrument substrate of FIG. 1B with a second polymer applied over a portion of the first polymer.

FIGS. 1A-1C illustrate an exemplary method of overmolding a plurality of polymers having different properties onto a dental instrument 100. The inventive method involves providing a dental instrument substrate 102 made of metal, as seen in FIG. 1A. A first polymer 104 is overmolded onto a portion of the dental instrument substrate 102, as seen in FIG. 1B. A second polymer 106 is then applied over a portion of the first polymer 104, as seen in FIG. 1C.

The first polymer 104 is overmolded over the dental instrument substrate 102 such that an exposed outer surface 108 of the first polymer 104 corresponds to a portion of the dental instrument 100 to be gripped within a collet of a dental hand piece for powered use. The second polymer 106 is applied over the first polymer 104 such that an exposed outer surface 110 of the second polymer 106 corresponds to a portion of the dental instrument to be gripped by a dental practitioner for manual use. According to one embodiment, the steps of overmolding a first polymer and applying a second polymer may be performed by injection molding, e.g., by a two-color injection molding process.

According to one embodiment, and as illustrated in FIG. 1C, the second polymer 106 may be applied so as to have an exposed outer surface 110 with a concave configuration. The concave configuration may provide increased gripability, while also preventing contact of the surface 110 with the collet of a powered handpiece, which may otherwise rip or tear the exposed outer surface 110.

Figure 2:
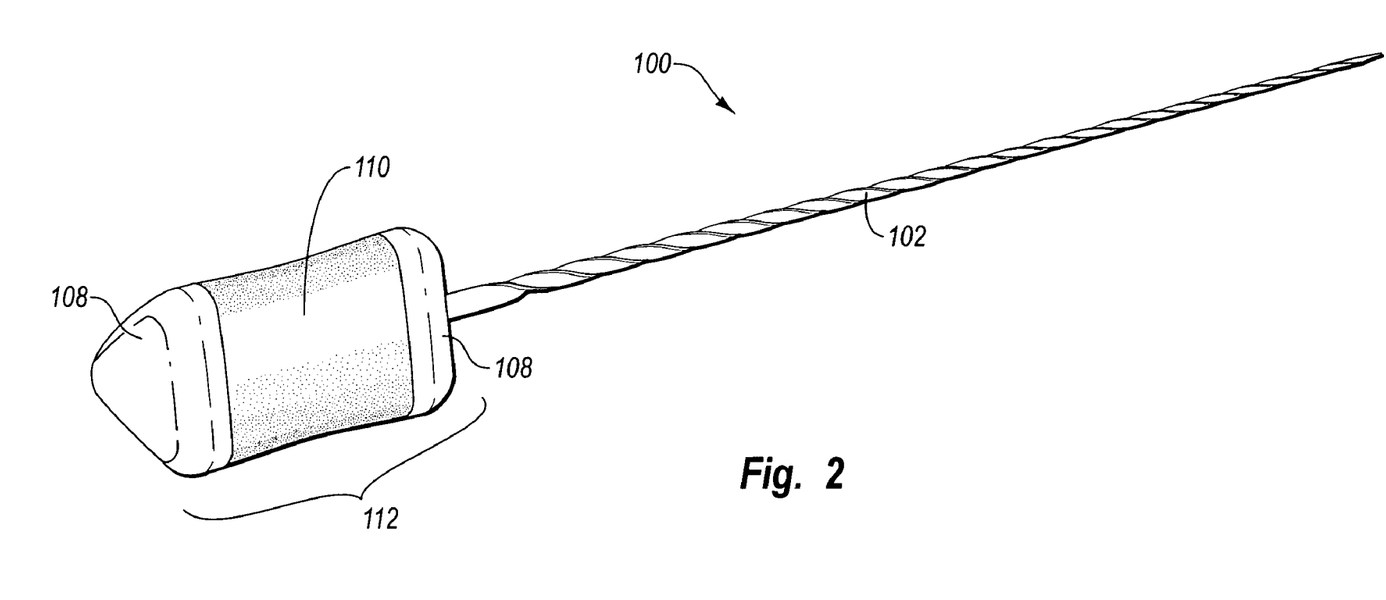
FIG. 2 is a perspective view of an exemplary dental instrument manufactured according to the method of the present invention.

FIG. 2 illustrates a perspective view of the dental instrument 100 of FIG. 1C. The instrument 100 includes a metallic dental instrument substrate 102. A handle 112 is provided at the proximal end of the metallic dental instrument substrate 102 in order to facilitate manual gripping of the dental instrument 100 by the dental practitioner or mechanical gripping by the dental hand piece (e.g., a reciprocating hand piece).

The handle 112 includes an overmolded first polymer and an applied second polymer. The first polymer includes an exposed outer surface 108 corresponding to a portion of the instrument 100 to be gripped within a collet of a dental hand piece. The second polymer includes an exposed outer surface 110 corresponding to a portion of the instrument 100 to be gripped by a dental practitioner during manual use.

The dental instrument of FIG. 2 includes a handle 112 having a trilobular cross section. A handle 112 having a trilobular cross sectional configuration is advantageous when manipulating the instrument by hand as it allows the dental practitioner to more easily apply the needed torque. In addition, a trilobular configuration provides improved gripability.

Figure 3:
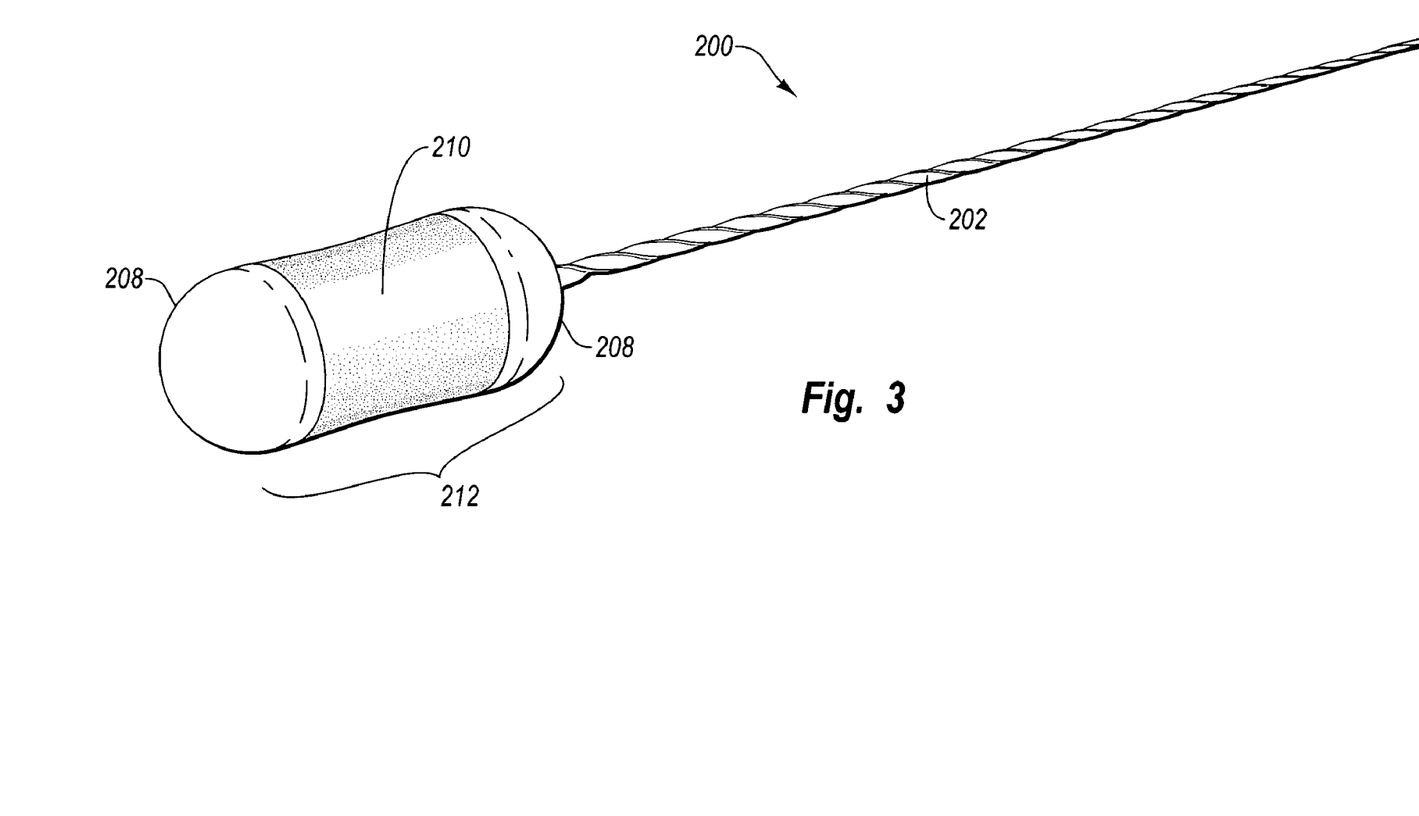
FIG. 3 is a perspective view of an alternative dental instrument manufactured according to the method of the present invention.

FIG. 3 is a perspective view of an alternative embodiment of a dental instrument 200 that includes a dental instrument substrate 202 and a handle 212, which includes an overmolded first polymer and an applied second polymer. The first polymer includes an exposed outer surface 208 corresponding to a portion of the instrument 200 to be gripped within a collet of a dental hand piece. The second polymer includes an exposed outer surface 210 corresponding to a portion of the instrument 200 to be gripped by a dental practitioner during manual use. The handle 212 of dental instrument 200 has a circular cross section. As illustrated, the outer surface 210 may be characterized by a concave curvature.

The outer surfaces 208 and 210 are configured to have specific properties. According to one embodiment, the first polymer comprising outer surface 208 may be a rigid polymer material. A rigid polymer material provides strength and durability, which is important for portions of the dental instrument that will be subjected to stresses and forces associated with gripping the instrument within the collet of a dental hand piece. Strength and durability will prevent these portions of the dental instrument from cracking or being deformed under stress.

According to one embodiment, the rigid polymer material may comprise any rigid thermoplastic material. Suitable rigid thermoplastics include polycarbonates, acrylonitrile butadiene styrene, polyamides, acetals and polysulfones. According to another embodiment, the rigid polymer material may comprise a rigid chemical cure or thermocure polymer material. Besides providing rigidity, strength, and durability, a chemical cure or thermocure polymer material also provides the advantageous characteristic of being autoclavable. Exemplary rigid chemical cure or thermocure polymers include epoxies, phenolics, acrylates, urethanes and polyesters.

According to one embodiment, the second polymer comprising outer surface 210 may be an elastomeric material. An elastomeric material provides increased comfort and grippability to portions of the dental instrument that are gripped by a dental practitioner when using the dental instrument manually. According to one embodiment, the elastomeric polymer material may comprise a thermoplastic elastomer. Alternatively, the elastomeric polymer material may comprise an elastomeric chemical cure or thermocure polymer material for the added advantage of autoclavability.

Examples of suitable thermoplastic elastomers include SARLINK (which comprises EPDM (i.e., ethylene-propylene rubber) particles embedded in a polypropylene matrix), ENGAGE (a polyolefin elastomer), SANTOPRENE (a synthetic rubber), and J-VON (a synthetic rubber. Examples of suitable elastomeric chemical cure or thermocure polymers include silicone rubber, natural rubber, synthetic rubber, and lower durometer urethanes.

The resulting dental instrument includes portions having characteristics of rigidity, strength, and durability, and other portions having characteristics of elasticity, comfort, and grippability. These characteristics allow the dental instrument manufactured according to the inventive method to be used advantageously with a powered hand piece or manually, as desired.

Figure 4A:
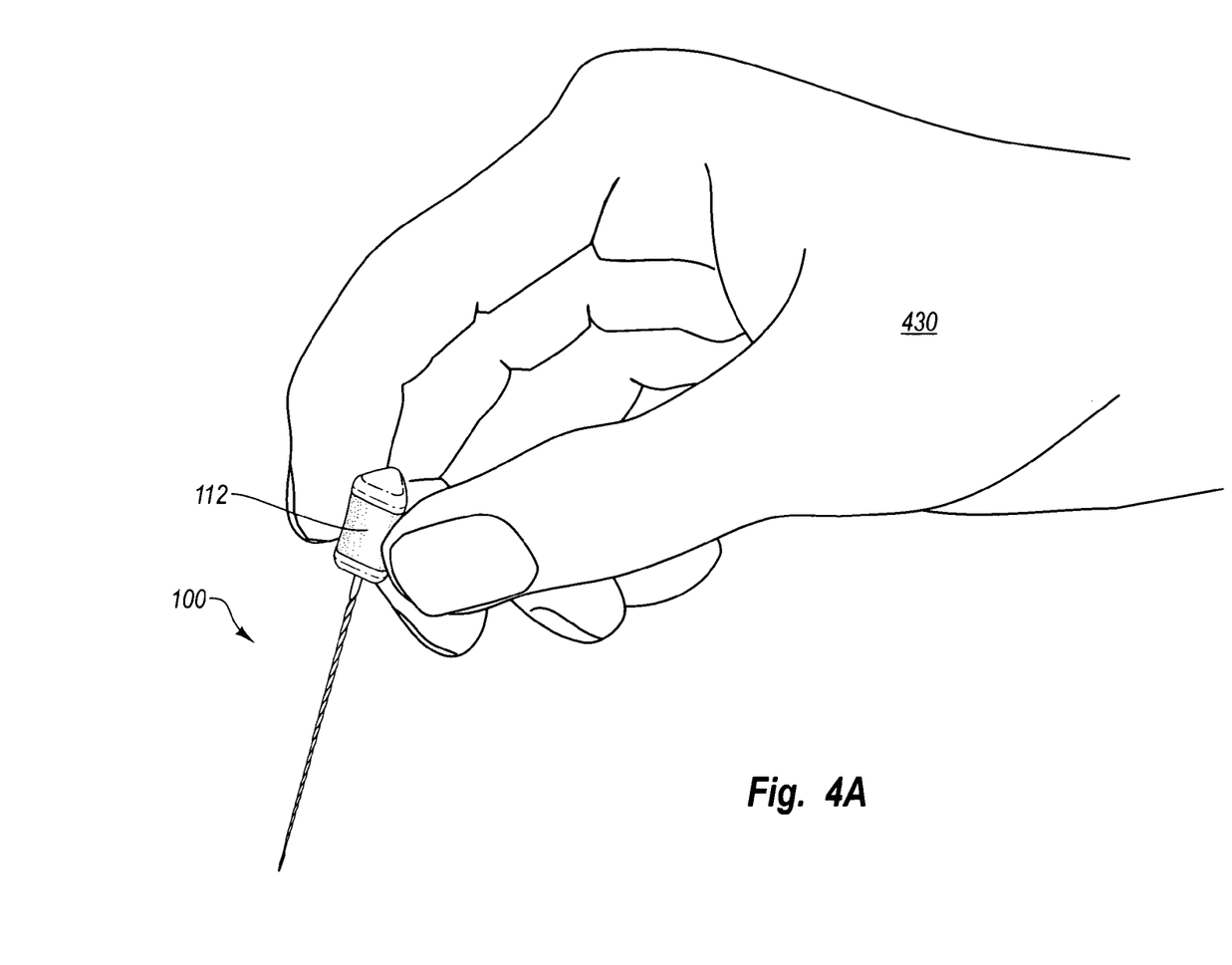
FIG. 4A is a perspective view of the dental instrument of FIG. 2 being held within the hand of a dental practitioner.

FIG. 4A illustrates dental instrument 100 being gripped manually by a dental practitioner's hand 430. The trilobular configuration of handle 112 allows the dental practitioner to more easily apply the needed torque during use.

Figure 4B:
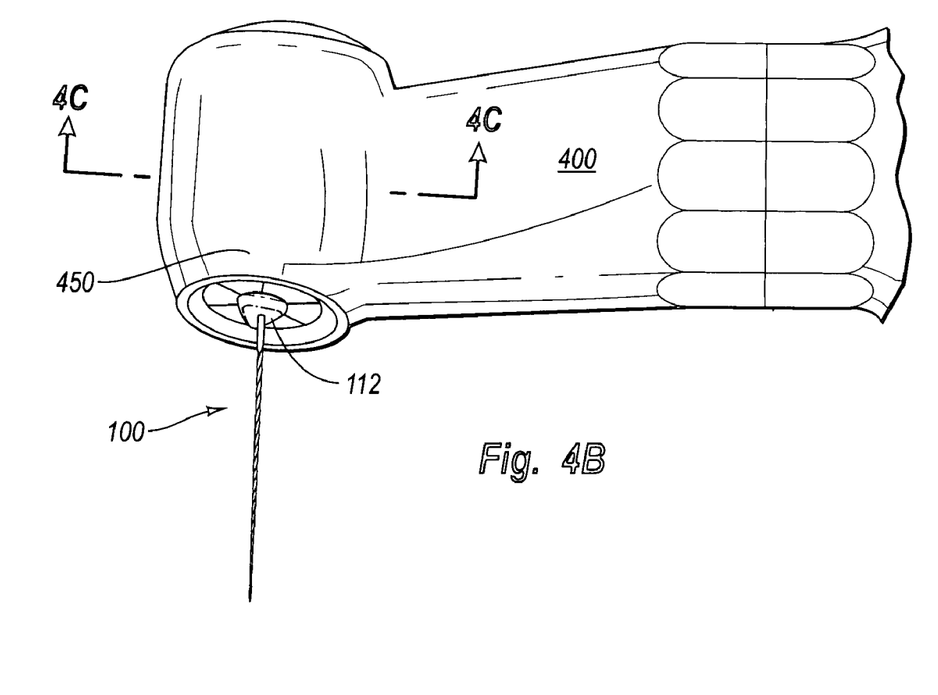
FIG. 4B is a perspective view of the dental instrument of FIG. 2 being held within a collet of a powered hand piece.
Figure 4C:
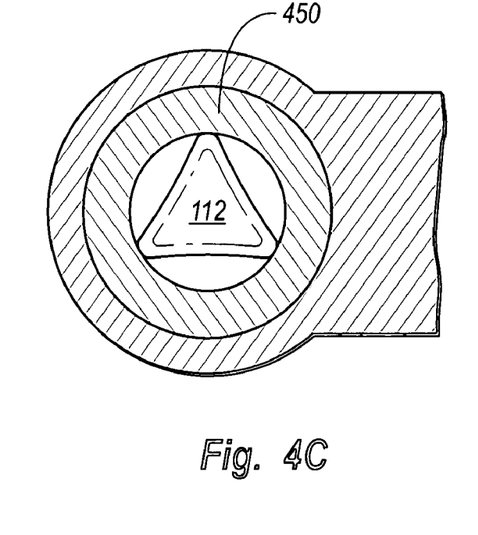
FIG. 4C is a cross sectional view of the dental instrument and powered hand piece of FIG. 4B taken along cutting line 4C-4C.

Referring to FIGS. 4B and 4C, a trilobular handle configuration is also suitable for use within a powered hand piece. FIG. 4B illustrates dental instrument 100 having a trilobular handle 112 received within a collet 450 of a powered hand piece 400. As best seen in FIG. 4C, the lobes of the handle 112 are received within and securely held by the (e.g., round) collet 450 of the hand piece 400. The exposed outer surface 110 of the relatively soft second polymer is not in gripping contact with the collet 450 of the handpiece 400, which might otherwise tear, rip, or deform the relatively soft second polymer.

According to one embodiment, the dental instrument 100 manufactured according to the inventive method may be autoclavable. This may be accomplished according to one embodiment by selecting first and second polymers that are chemically or thermally curable and that have melting and decomposition temperatures that are significantly greater than autoclaving temperatures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for overmolding a plurality of polymers having different properties onto a dental instrument that is adapted for both mechanical and manual manipulation, the method comprising:
providing a dental instrument substrate made of metal;
overmolding a first polymer onto a portion of the dental instrument substrate so as to form a first portion of a handle; and
applying a second polymer over a portion of the first polymer so as to form a second portion of the handle that is less rigid and more flexible than the first portion,
wherein the handle has a first end surface, a second end surface, and a side surface disposed between the first and second end surfaces,
wherein the first polymer has an exposed outer perimeter that defines a portion of the side surface of the handle and wherein the second polymer has an exposed outer perimeter that defines another portion of the side surface of the handle, the exposed outer perimeters of the first and second polymers being substantially even where they make abutment on the side surface of the handle,
wherein the exposed outer perimeter of the first polymer provides an exposed surface of the handle not covered by the second polymer that is grippable by a collet of a dental hand piece without obstruction by the second polymer, and
wherein an exposed outer surface of the second polymer enhances manual grip by a dental practitioner.

2. A method as recited in claim 1, wherein the steps of overmolding a first polymer onto a portion of the dental instrument substrate and applying a second polymer over a portion of the first polymer comprise a two-color injection molding process.

3. A method as recited in claim 1, wherein the first polymer comprises a rigid polymer material.

4. A method as recited in claim 3, wherein the rigid polymer material comprises a rigid thermoplastic polymer.

5. A method as recited in claim 4, wherein the rigid thermoplastic polymer comprises at least one member selected from the group consisting of polycarbonates, acrylonitrile butadiene styrene, and polyamides.

6. An article of manufacture comprising a dental instrument manufactured according to the method of claim 5.

7. A method as recited in claim 3, wherein the rigid polymer material comprises a rigid chemical cure or thermocure polymer, the method further comprising curing the first polymer.

8. A method as recited in claim 7, wherein the rigid chemical cure or thermocure polymer comprises at least one member selected from the group consisting of epoxies, phenolics, acrylates, urethanes, and polyesters.

9. An article of manufacture comprising a dental instrument manufactured according to the method of claim 8.

10. A method as recited in claim 1, wherein the second polymer comprises a thermoplastic elastomer.

11. A method as recited in claim 10, wherein the thermoplastic elastomer comprises at least one member selected from the group consisting of polyolefin-based elastomers and synthetic rubbers.

12. An article of manufacture comprising a dental instrument manufactured according to the method of claim 11.

13. A method as recited in claim 1, wherein the second polymer comprises an elastomeric chemical cure or thermocure elastomer, the method further comprising curing the second polymer.

14. A method as recited in claim 13, wherein the elastomeric chemical cure or thermocure polymer comprises at least one member selected from the group consisting of silicone rubber, natural rubber, synthetic rubber, and lower durometer polyurethanes.

15. An article of manufacture comprising a dental instrument manufactured according to the method of claim 14.

16. An article of manufacture comprising a dental instrument manufactured according to the method of claim 1.

17. An article of manufacture comprising a dental instrument as recited in claim 16, wherein the dental instrument substrate made of metal comprises an endodontic file.

18. An article of manufacture comprising a dental instrument as recited in claim 16, wherein the first polymer and the second polymer form a trilobular handle.

19. An article of manufacture comprising a dental instrument as recited in claim 16, wherein the dental instrument is autoclavable without melting or decomposing the first and second polymers.

20. A dental instrument adapted for both manual use and powered use, comprising:
a dental instrument substrate made of metal; and
a handle formed at an end of the file shank and having a first end surface, a second end surface, and a side surface disposed between the first and second end surfaces, wherein the handle is comprised of:
a rigid polymer formed over a portion of the dental instrument substrate, the rigid polymer having an exposed outer perimeter that extends along a portion of the side surface of the handle so as to provide a continuous surface that is grippable by a collet of a dental hand piece for powered use; and
a flexible polymer formed over a portion of the rigid polymer, the flexible polymer having an exposed outer perimeter that facilitates manual gripping of the handle and which is substantially even with the exposed outer perimeter of the rigid polymer where the flexible polymer and rigid polymer make abutment at the side surface of the handle so as to not obstruct gripping of the exposed outer perimeter of the rigid polymer by a collet of a dental hand piece.

21. A dental instrument as recited in claim 20, the first and second polymers forming a trilobular handle.

22. A dental instrument as recited in claim 20, the first and second polymers forming a handle having a substantially circular cross section.

23. A dental instrument as recited in claim 20, the first and second polymers both having melting and decomposition temperatures above autoclaving temperatures.

24. An endodontic file apparatus adapted for use in performing an endodontic procedure within a root canal of a tooth, comprising:

an endodontic file shank made of metal; and a handle formed at an end of the file shank and having a first end surface, a second end surface, and a side surface disposed between the first and second end surfaces, wherein the handle has is comprised of:

a rigid polymer formed over a portion of the endodontic file shank and having a first exposed outer surface that forms a first outer perimeter of a first portion of the side surface near the first end surface of the handle and a second exposed outer surface that forms a second outer perimeter of a second portion of the side surface near the second end surface of the handle; and a flexible polymer formed over a portion of the rigid polymer, the flexible polymer having an exposed outer surface that extends continuously between the first and second exposed outer surfaces of the rigid polymer and facilitates manual gripping of the handle.

* * * * *

UNITED STATES PATENT AND TRADEMARK OFFICE
CERTIFICATE OF CORRECTION

| | | |
|---|---|---|
| PATENT NO. | : 7,226,289 B2 | Page 1 of 1 |
| APPLICATION NO. | : 10/996100 | |
| DATED | : June 5, 2007 | |
| INVENTOR(S) | : Dan J. Bills | |

It is certified that error appears in the above-identified patent and that said Letters Patent is hereby corrected as shown below:

Column 4
Line 44, change "(a synthetic rubber." to --(a synthetic rubber).--

Column 7
Line 8, delete "has"

Signed and Sealed this

Twenty-seventh Day of November, 2007

JON W. DUDAS
*Director of the United States Patent and Trademark Office*